United States Patent [19]
Bolton et al.

[11] Patent Number: 4,857,747
[45] Date of Patent: Aug. 15, 1989

[54] METHOD AND APPARATUS FOR ANALYZING THE FORMATION OF A WEB OF MATERIAL VIA GENERATING A FORMATION INDEX

[75] Inventors: Joseph A. Bolton, Queensbury, N.Y.; Steven K. Harbaugh, Castro Valley, Calif.

[73] Assignee: Albany International Corporation, Menands, N.Y.

[21] Appl. No.: 159,830

[22] Filed: Feb. 24, 1988

[51] Int. Cl.⁴ ............................................. G01N 21/86
[52] U.S. Cl. ..................................... 250/559; 250/563; 356/431
[58] Field of Search ............... 250/559, 560, 561, 562, 250/563, 571, 572; 356/430, 431, 444

[56] References Cited

U.S. PATENT DOCUMENTS

| | | | |
|---|---|---|---|
| 3,479,518 | 11/1969 | Akamatsu et al. | 250/219 |
| 3,498,719 | 3/1970 | Wing et al. | 356/36 |
| 3,835,332 | 9/1974 | Bridges | 250/563 |
| 3,859,538 | 1/1975 | Mannonen | 250/572 |
| 3,968,006 | 7/1976 | Zimmerman | 162/198 |
| 4,019,066 | 4/1977 | Lucas et al. | 250/562 |
| 4,040,743 | 8/1977 | Villaume et al. | 356/73 |
| 4,092,068 | 5/1978 | Lucas et al. | 356/73 |
| 4,171,916 | 10/1979 | Simms et al. | 356/366 |
| 4,402,604 | 9/1983 | Nash | 356/237 |
| 4,490,618 | 12/1984 | Cielo | 250/571 |
| 4,511,803 | 4/1985 | Röss et al. | 250/563 |
| 4,522,497 | 6/1985 | Ikin | 356/431 |
| 4,574,624 | 3/1986 | Lehtinen et al. | 73/63 |
| 4,644,174 | 2/1987 | Ouellette et al. | 250/559 |
| 4,648,712 | 3/1987 | Brenholdt | 356/73 |

Primary Examiner—David C. Nelms
Assistant Examiner—William L. Oen
Attorney, Agent, or Firm—Kane, Dalsimer, Sullivan, Kurucz, Levy, Eisele and Richard

[57] ABSTRACT

A method and apparatus for generating in real time full width formation profiles of a web of material which passes between a light source and a camera which generates signals corresponding to the light intensity across the entire width of the web as compared to single point or sample measurements. These signals are then processed to generate in real time at a full width formation profile of the web.

9 Claims, 2 Drawing Sheets

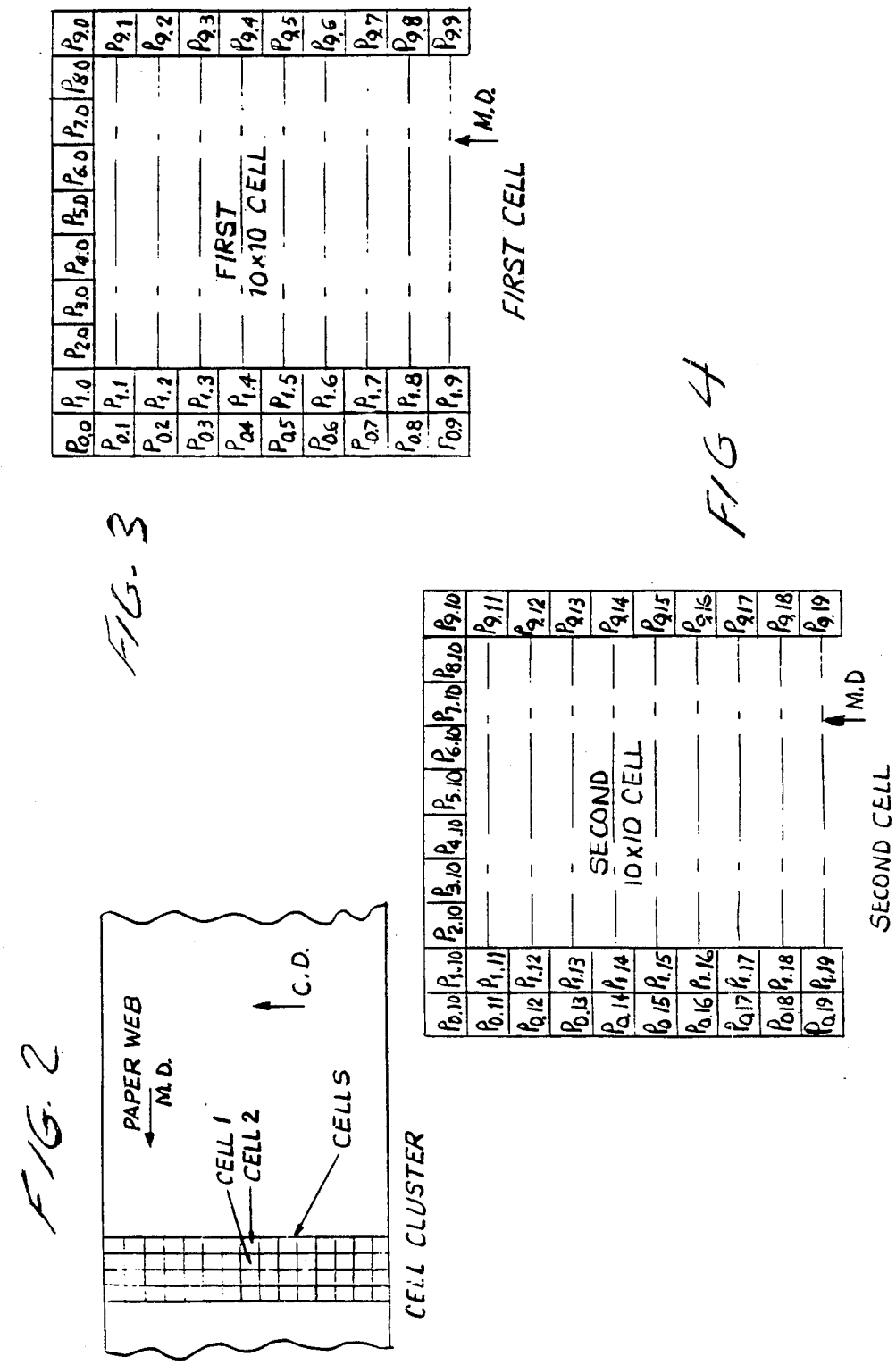

METHOD AND APPARATUS FOR ANALYZING THE FORMATION OF A WEB OF MATERIAL VIA GENERATING A FORMATION INDEX

BACKGROUND OF THE INVENTION

In the nonwoven and paper industries, webs of material are produced at very high rates of speed. An important consideration in such manufacture is the monitoring of the formation of the web. The quality of the non-woven paper material is always important to the quality of the end product produced.

Formation to most web manufacturers is the degree of uniformity achieved in the distribution of the fiber mass within the web. A well formed web is one where the fibers are very randomly dispersed throughout. Well formed webs are usually stronger and have better appearance, which is important to the end user.

Good formation is especially important to nonwoven and paper manufacturers. Poor formation not only adversely effects a web or sheet appearance, but also effect its printability and other qualities.

The traditional methods of classifying the formation of nonwoven webs and paper sheets has been with human inspection and off-line formation sensors. The describing of a given web or sheet as being good, not bad, floccy, streaky, etc., is very relative and subjective. Studies in general have shown very poor agreement between visual and off-line formation sensors.

The problems with off-line formation sensors is the time between sample and results and also obtaining good profile measurements. At the speeds most modern nonwoven and paper manufacturers run thousands of yards of material can be off quality before the results from the lab are obtained.

Studies made of variations in formations of paper webs has shown more variations across the web versus downweb. Therefore, the need for continuous updating of formation profile measurements is important.

To help eliminate the problems with human inspection of webs and the use of off-line sensors, manufacturers are starting to use single point formation sensors on-line. Some are fixed on the machine while others are slowly traversed across the web. Most of these sensors use the principle of comparing the light intensity of a small area 1 mm or less with a larger area, say of 30 mm dia. or larger. A formation index is based upon the intensity variation in the small area as compared to the average light intensity of the larger area.

The problem to date with these on-line single point formation sensors has been with the repeatability of the results with changing machine speeds and products. Another problem has been in getting rapid formation profile measurements across the web in less time than for example a minute of operation.

A further improvement to these on-line single point formation sensors is the use of a linear array CCD (charged coupled device) camera which looks at the variations in light intensities across the entire moving web without traversing. This technology has an outgrowth of using linear array CCD cameras to inspect for defects in moving webs. Defects like holes or dark spots would cause the light intensity at a given area in the web to exceed from its normal range and cross a given light or dark threshold, thus signaling a defect has been detected. One such system is being marketed by Albany International, assignee of the present application, under the name WEBSPEC TM.

In such a system an automatic, high-speed visual web inspection system is provided. A full web width high-intensity light source is used to shine through the moving web. A linear CCD camera with a zoom lens is focused on the streak of light passing through the web. The camera contains a given number of solid-state, photo-sensitive devices used to detect the variation in light intensities across the web. An analog electrical signal, proportional to the light intensity detected by the respective photo-sensitive devices, is sent to the computer system. Normally, all the photo-sensitive devices in the camera are used to scan the web once. Therefore, if the camera contains 2,048 devices, the number of picture elements or "pixels" per scan would equal 2,048.

The analog signals from the devices are converted to digital for binary and digital image analysis by the computer system. The analog signals from the camera are normalized, compared to threshold settings and processed with a 68000 microprocessor. An information summary on the type, size and location of the defects detected can be either stored on disk or a hard copy made using a printer and a flagger is activated to place a flag adjacent a defect in the downweb direction.

While such a defect identifier has proven eminently satisfactory for defect detection, another aspect of web analysis involves as aforenoted that of the formation of the web. The formation quality of paper is defined as the degree of uniformity achieved in the distribution of fiber mass. A well formed sheet is one where the fibers are very randomly dispersed throughout the entire sheet. Good formation is essential during papermaking because it strongly affects the appearance and printability of the sheet. In general, poor formation adversely effects other sheet qualities. Well formed paper is stronger, more uniform, easier to dry and allows the paper machine to run better.

Describing a given paper sample or sheet as good, not bad, poor, floccy, streaky, etc., indicates that formation is very subjective. Studies by The Institute of Paper Chemistry (Paper Trade Journal, May 30, 1984) concluded that reproducibility of visual formation gradings between different observers was relatively poor. A better formation grading was obtained between a Thwing-Albert formation tester and the average of the visual results.

Because of these difficulties and the importance of good formation to the papermaker, an effort has been made to develop a so called "standard formation tester of sensor" which could be used either on or off line. Some of the testers developed over the years include the QNSM, NUI, MKS, Thwing-Albert, Microscanner TM, Toyoseiki, Lippke and more recently the Opti Pak TM. All have been used for papermakers to help quantify the formation they were obtaining and to make quality improvements.

However there exists a need for a full width real time formation sensor for paper machine applications which has not heretofore been achieved. This is especially true, since on most paper machines, variation in formation across the web (C.D. or X.D.) is much greater than in the downweb direction. Therefore the need for full width formation measurements versus single point or sample measurements heretofore utilized is clear.

SUMMARY OF THE INVENTION

Accordingly, it is a principal object of the invention to provide a method and apparatus for a full width formation system for web analysis.

It is a further object to provide for such a system which is on line which gives full width formation indexes in real time.

It is a yet further object to provide for such a system which is particularly applicable to the papermaking industry.

It is yet a further object to provide for such a full width real time system which includes the following features:

provides results that correlate with visual inspection;
provides results that are repeatable without the need to do any calibration adjustments;
provides results that are independent of machine speed variations;
may be used on any grade of paper where formation is important;
it is dependable and readily adjusted to suit a given product or grade; and
have the ability to store data such that trends, averages and statistical analysis can be performed.

Such objects are achieved by the present invention which is currently being marketed as the FORM-SPEC TM system by Albany International. Basically the system involves the use of a linear array CCD camera to measure the variation of transmitted light through a moving web. The light intensities across the entire web are converted into analog electrical signals and inturn digital signals. Such signals are connected within a minimum and maximum range which may for example be between a level of 0 to 255. The analog signals from the elements would then be converted to digital values of between 0 and 255, depending upon the DC voltage generated by the elements. The number of pixels used in the camera will depend upon the particular application. Typically these would be 1K, 2K or 4K line scan cameras. For example, if the camera contains 2,048 elements, the number of picture elements or pixels per scan would equal 2,048.

The linear array CCD camera is effective in determining differences in the formation of the paper web. A formation index is generated from the information generated by electronic scanning. The variation of light intensity of each pixel is 0–256 which is a relative number and which is normalized for purposes of compensating for changes in B.W. and color, in addition to changes in intensity of the light source from one end to the other. The system continuously normalizes itself to compensate for static or dynamic variations in light intensity, such that the average or base line intensity is relatively constant.

The system measures the light intensity for each pixel at various locations or positions within a predetermined segment or scan subdivided into cells. Each pixel value within each cell are determined compared to one another with all the absolute differences therebetween determined and added up to achieve a value. The average pixel intensity for pixels within the cells is determined and is divided into this value.

It should be noted that a major difference between a web inspection system and a web formation sensor, both using a linear array CCD camera, is the inspection system only analyzes defect areas which cross the light intensity threshold limits. In a formation measuring system, all light intensity variations are measured for a given area and not just areas that exceed threshold limits.

Another difference between an inspection and a formation measuring system is basically in the method used to process the data obtained. With an inspection system one wants to known the following:

(a) Type of defect (light or dark)?
(b) How big is it?
(c) Where is it located across the web?
(d) Where is it at any time up web for flagging?

However, with a formation measuring system, one is not looking for any single defects in a moving web, but rather is continuously measuring the small variations in light intensities of small areas all across the moving web. The size of the small areas measured depends upon the type of web to be analyzed. For example, for paper webs the size of the pixel elements across web should be between 1.0 and 2.5 mm wide. Downweb the pixel size or distance between scans should be between 1.0 and 5.0 mm. As compared, on nonwoven applications, the size of the pixel elements across web will be much larger than required for paper applications. Therefore, on nonwoven applications, the pixel elements across web should be between 2.0 and 25 mm.

Thus, it is readily apparent that these systems while operative on the same web, do so in a different manner and for a different purpose, to obtain different results.

The formation inspection provided by the present invention is clearly distinct from any defect inspection and provides a vast improvement over prior method of inspection in this regard.

BRIEF DESCRIPTION OF THE DRAWING

Thus by the present invention, the aforenoted objects and advantages will be realized, the description of which should be taken in conjunction with the drawings, wherein:

FIG. 2 indicates a schematic representation of a cell cluster information index analysis;

FIG. 3 indicates a breakdown of the individual cells making up the cell cluster of FIG. 2; and FIG. 4 represents the formation index generation analysis.

DETAILED DESCRIPTION OF THE DRAWINGS

Figure 1:
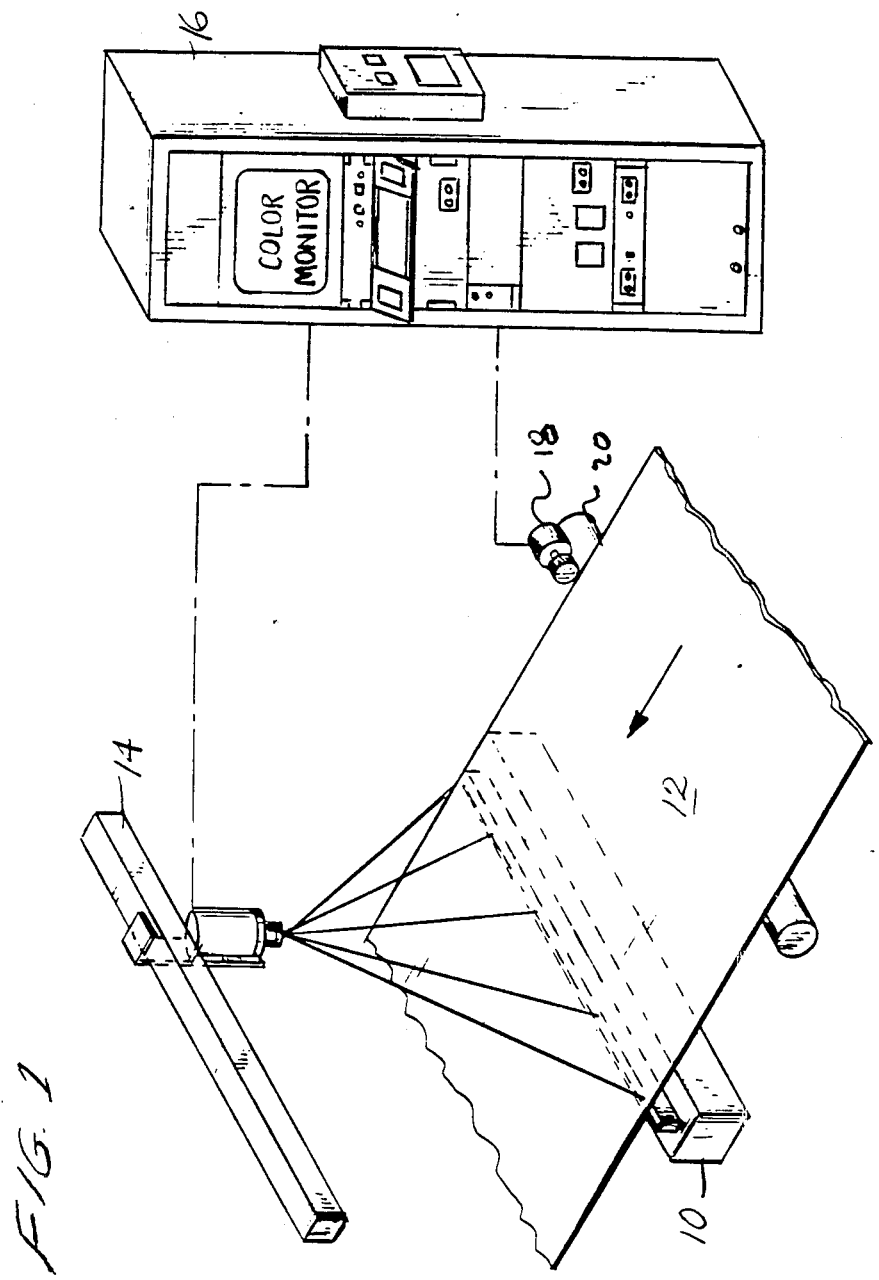
FIG. 1 is a perspective somewhat schematic view of the system incorporating the teachings of the present invention.

Turning now more particularly to the drawings, a high intensity light source 10 is used to transmit a narrow beam of light through the entire width of the moving web 12 of paper. The intensity of the light source is normally four or five times brighter than a standard fluorescent tube and is very uniform from end to end.

A linear array CCD camera 14 is provided to continuously sense and measure the variations in light intensities over the entire web width. To monitor the entire moving web, the CCD camera is preferably installed at a height above the web equal to approximately 1.4 times the web width depending upon the focal length lens used. The analog output signals from the camera are converted to digital values for analysis by a computer and monitor console generally designated as 16. A motorola 68000 microprocessor has been found suitable for the processing purposes.

In many applications a 2K camera having a maximum scan rate of 5,000 scans per second will be sufficient. The formation measurements would then be based upon 10 million measurements per second. This is approximately 100 times greater than the typical on line formation sensor being used today. The scanning rate of the camera can be regulated so as to correspond to various speeds of the web by way of a tachometer or pulse generator 18 coupled to a roller 20 engaging the web 12. The faster the speed of the web 12, the faster the scanning rate and vice versa.

The computer system and color monitor in the console 16 calculate formation information, and display profiles, trends and averages. Historical data is stored for further analysis or downloading.

At this point, it may be beneficial to review just what is involved in a CCD camera used in the system. The typical linear array CCD camera uses an array of either 1024, 2048, or 4096 solid-state, photo-sensitive elements. These are often referred to as 1K, 2K or 4K line scan cameras. Each photo-sensitive element is very small, only approximately 13 microns square or 0.0005 inches. All the elements are contained in an array approximately 2.5 cm or 1 inch long. The elements are used to measure the variation in light intensities across the web. An analog electrical signal proportional to the light intensity detected by an element is sent to a computer system for processing. Normally all the elements in the camera are used to scan the web once. Therefore, if the camera contains 2,048 elements, the number of pixels per scan would be 2,048 and so forth.

The value assigned is directly proportional to the total amount of light seen by each element with 0 value for minimum light and 256 for maximum intensity. In other words, each element can detect up to 255 different levels of light intensity.

In developing a formation sensor system, the following factors should be considered in the example to be given:

The minimum cross web measurement interval for formation profiles is 2.54 cm.;

Maximum dynamic speed variation for any given paper grade will be less than two to one;

The floc size for a given product remains relatively constant;

Measurements requiring high resolutions to detect paper sensitivity to wire marks are not necessary;

Machine speeds will normally be within the 300 to 1,200 meters/minute range;

A formation profile update every 30 to 60 seconds is sufficient for most applications;

The CCD camera can be and is located within 40 meters of the console;

Machines will have access for back illumination of the web and room to mount camera; and Web widths greater than 6 meters will require more than one CCD camera.

As noted, the system is looking at the entire web all the time. Each time a camera scan is indicated, the system records the variations in light intensities over 2,048 elements across the web, using a 2K camera. This means with a 5 meter wide web, each element would be approximately 2.5 mm. wide. With a maximum scan rate of 5,000 times per second, the downweb pixel size would also be 2.5 mm. long at machine speeds up to approximately 760 meters/minute. At machine speeds greater than this, the downweb pixel size would be greater.

As to how a formation index is calculated, as shown in FIG. 2 the individual pixels are grouped into cells. Each cell may contain 8, 10, etc. pixels across web by 8, 10, etc. scan lines long. The size of a cell, both across and downweb, is a variable depending upon a given paper grade.

For example, with a 10 by 10 pixel cells as shown in FIG. 3, it has an overall dimension of approximately 2.5 by 2.5 cm. As previously stated, the system is able to measure up to 256 different levels of light intensities. These levels are only relative measurements of light intensities. The system normalizes each pixel to take care of changes in B.W. and color of the sheet plus any difference in the intensity of the light source from end to end. Therefore, the system is continuously normalizing itself to take care of static or dynamic variations in light intensities through the sheet such that the average or base line intensity is relatively constant. What the formation system is doing is measuring the variations in light from an average value.

A formation index is calculated for a given web segment by the following method. Using the pixel values given in two 10 by 10 cells one right after the other in the downweb direction as shown in FIG. 2, a matrix notation $P_{i,j}$ is used to identify the given pixels in the cell. The subscript i refers to the pixel location in a given column, with j referring to the location in a given row. Therefore, pixel $P_{o,9}$ location would be the one located in column o, row 9 after the initial scan or row as shown in FIG. 3.

The method for calculating the formation index of a web segment is shown in association with FIG. 4. In association with the algorithm $FI = |P_{o;o} - P_{o;10}| + |P_{o;1} - P_{o;11}|$ through $|P_{o;9} - P_{o;10}|$ continuing to $|P_{9;9} - P_{9;19}|$ divided by $P_{ave}$ of $P_{o;o}$ through $P_{9;19'}$ all the absolute differences in light intensities are added comparing the same pixel location between the two different cells and dividing the results by the average intensity of all the pixels within the two cells. The formation index calculated is a rough approximation of the RMS of variations in light intensities. This procedure is repeated in this example say ten times within the same web segment and the resulting formation index average is then reported for that segment. The same calculations or procedures are done for all the other web segments across the web.

The number of formation index measurements across the web depends upon cell size and web width. For a 5 meter wide web with 2000 pixels per scan, (10 pixels across per cell, 200 cells) approximately 200 formation index measurements across the web per profile display would exist. This is sufficient cross web resolution for most paper machines since the typical distance between slice adjustments on most headboxes is around 15 cm. The formation index measurements may be every 2.5 cm.

The system will update the formation profile of a given web approximately every 30 seconds or at any other interval desired. Along with profiles, the monitor will also display targets, averages and trends. If desired, the system may down load this formation profile information to a mill wide computer system for further analysis. The system also has the potential for the mill for close loop control of formation.

Thus by the present invention, its objects, advantages and others are realized and although a preferred embodiment has been disclosed and described in detail herein, its scope should not be limited thereby, rather its scope should be determined by that of the appended claims.

What is claimed is:

1. A method of analyzing a web of material for generating a formation index comprising the following steps:

providing a light source on one side of the web of material for shining a light through the entire width of the web at a predetermined location;

providing a sensor comprising at least one camera at a predetermined distance from the web of material on the opposite side of that of the light source;

scanning the entire width of the web across a path defined by the light source with said camera to sense and measure variations in light intensities in a pixel by pixel basis across said width;

generating signals which correspond to the light intensity detected by said camera at respective pixels across said web width;

assigning a predetermined value level within a predetermined range for said respective signals corresponding to said pixel locations;

normalizing each pixel to compensate for static or dynamic variations in light intensities through the web of material;

determining an average light intensity at predetermined locations across the web and calculating a formation index based upon adding the absolute differences in light intensity at the same pixel locations on successive scans and dividing the results by the average light intensity for said predetermined location; and generating a formation index for the entire width of the web by successive calculation of formation indexes taken across said web of material at successive predetermined location.

2. The method in accordance with claim 1 wherein the rate at which the camera means scans is adjusted to the speed of the web.

3. The method in accordance with claim 1 which includes calculating the formation index by the following steps:

dividing the scanning area of the camera across the web into web segments;

dividing the web segments into a cluster of cells;

dividing the cluster into subdivisions of successive cells which follow one after the other along the scan line as the web moves thereacross, said cells comprising a predetermined number of pixels;

determining the sum of the absolute values of respective pixels for respective successive cells and the average value for all the pixels in said cells to generate a formation index; and generating a formation index for all the cells in the cluster and for all the clusters in the web segment to generate in real time a formation index across the entire width of the web.

4. The method in accordance with claim 1 which includes the step of providing a sensor comprising a linear array CCD camera.

5. A system for generating a formation index in real time for the full width of a web of material, comprising:

a light source for shining a light on one side of a web of material passing thereover at a predetermined location;

a sensor means comprising a camera means positioned at a predetermined distance from the web of material on the opposite side thereof then that of the light source;

said camera means function to scan across the full width of the web across a path defined by the light source to measure the variations in light intensities over said width and generate signals which correspond to the light intensity detected at respective predetermined pixel positions in the web;

processor means for receiving said signals and processing said signals in real time to generate a formation profile for the full width of the web at predetermined intervals as said web passes said sensor means; and display means for displaying electronically in real time the formation profile of the web.

6. The invention in accordance with claim 5 which includes pulse generator means for generating a signal corresponding to the speed of the web for adjusting the rate of scan of the camera means of the web.

7. The invention in accordance with claim 5 wherein the processor means in conjunction with the sensor means divides electronically sections of the web during the scanning thereof into web segments which in turn are broken down into cell clusters, cells and respective pixels for the respective cells; said camera means generates a signal on each scan for each respective pixel corresponding to the light intensity thereof and said processor means uses said signals and signals from respective scans to generate a formation index for the respective cells, cell clusters, web segments and the entire width of the web.

8. The system in accordance with claim 5 wherein said camera means comprises a linear array CCD camera.

9. The system in accordance with claim 3 wherein a formation index based upon adding the absolute differences on adjacent pixels within a given cell and divide the results by the average light intensities of the cells being compared.

* * * * *